US00PP36028P2

(12) United States Plant Patent
Ackerman et al.

(10) Patent No.: US PP36,028 P2
(45) Date of Patent: Jul. 23, 2024

(54) STRAWBERRY PLANT NAMED 'PS-14.762.054'

(50) Latin Name: *Fragaria ananassa*
Varietal Denomination: PS-14.762.054

(71) Applicant: Plant Sciences, Inc., Watsonville, CA (US)

(72) Inventors: Stephen M. Ackerman, Salinas, CA (US); Steven D. Nelson, Watsonville, CA (US); Michael D. Nelson, Watsonville, CA (US)

(73) Assignee: Plant Sciences, Inc., Watsonville, CA (US)

( * ) Notice: Subject to any disclaimer, the term of this patent is extended or adjusted under 35 U.S.C. 154(b) by 0 days.

(21) Appl. No.: 18/368,519

(22) Filed: Sep. 14, 2023

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208
See application file for complete search history.

(56) References Cited

U.S. PATENT DOCUMENTS

PP17,312 P2 12/2006 Ackerman et al.
PP21,415 P3 10/2010 Ackerman et al.

*Primary Examiner* — Susan McCormick Ewoldt
*Assistant Examiner* — Zachariah Allan Kay
(74) *Attorney, Agent, or Firm* — Foley & Lardner LLP

(57) ABSTRACT

This invention relates to a new and distinct variety of strawberry plant named 'PS-14.762.054'. This new strawberry plant named 'PS-14.762.054' is primarily adapted to the growing conditions of the central coast of California, and is primarily characterized by its red fruit color, large fruit size, conical fruit shape with no to very slight differences between primary and secondary fruit; with seeds held even with the fruit surface; very early fruiting plant, medium plant size, upright in habit, with a slightly open canopy; medium yellow green foliage color, large in size with three leaflets; fruiting trusses typically held level to beneath the foliage, with weak pubescence and strong anthocyanins; and resistance to *Fusarium* wilt.

5 Drawing Sheets

Latin name of the genus and species of the plant claimed: *Fragaria ananassa.*

Variety denomination: 'PS-14.762.054'.

BACKGROUND OF THE INVENTION

The present invention relates to a new and distinct strawberry variety named 'PS-14.762.054'. This new variety is a result of a controlled cross made in 2014 in an ongoing breeding program between strawberry selection designated 'PS-8.1116' (unpatented) as the seed (female) parent, and strawberry variety designated 'PS-5016' (U.S. Plant Pat. No. 17,312) as the pollen (male) parent. The variety is botanically known as *Fragaria ananassa.*

The seedling resulting from the aforementioned cross was selected from a controlled breeding plot in Monterey County, California in the summer of 2016. After its selection, the new variety was asexually propagated by stolons in both Siskiyou County, California and San Joaquin County, California. The new variety was extensively tested over the next several years in fruiting fields in Monterey County, California. This propagation has demonstrated that the combination of traits disclosed herein as characterizing the new variety are fixed and remain true-to-type through successive generations of asexual reproduction.

BRIEF SUMMARY OF THE INVENTION

'PS-14.762.054' is primarily adapted to the climate and growing conditions of the central coast of California. The nearby Pacific Ocean provides the humidity and moderate temperatures needed to produce a strong, vigorous plant and maintain fruit quality during the spring and summer production months.

The following traits have been repeatedly observed and are determined to be unique characteristics of 'PS-14.762.054', which in combination distinguish this strawberry plant as a new and distinct variety:

1. Red fruit color, large fruit size, conical fruit shape with no to very slight differences between primary and secondary fruit;
2. Seeds that are held even with the fruit surface;
3. Very early fruiting plant, medium plant size, upright in habit, with a slightly open canopy;
4. Medium yellow green foliage color, large in size with three leaflets;
5. Fruiting trusses typically held level to beneath the foliage, with weak pubescence and strong anthocyanins; and
6. Resistant to *Fusarium* wilt.

The strawberry variety that is believed to be most closely related to the new variety 'PS-14.762.054' is 'PS-9271' (U.S. Plant Pat. No. 21,415). In side-by-side comparisons to the similar strawberry variety 'PS-9271', 'PS-14.762.054' differs by the following combination of characteristics as described in Table 1.

TABLE 1

| Characteristic | 'PS-14.762.054' | 'PS-9271' (U.S. Plant Pat. 21,415) |
|---|---|---|
| Fruit: color | Red | Ranges from red to dark red |
| Fruit: attitude of sepals | Ranges from outward to upward | Outward |
| Fruit: flavor | Very good | Good |
| Fruit: time of ripening | Very early | Medium |
| Plant: density | Ranges from medium to sparse | Medium |
| Foliage: color of upper surface | Medium yellow green | Medium green |
| Fruiting truss: Anthocyanin intensity | Strong | Ranges from medium to weak |

For identification, a series of molecular markers have been determined for this new variety.

'PS-14.762.054' differs from its parents, 'PS-8.1116' and 'PS-5016' by the following combination of characteristics as described in Tables 2 and 3.

TABLE 2

| Characteristic | 'PS-14.762.054' | 'PS-8.1116' (unpatented) |
|---|---|---|
| Fruit: color | Red | Ranges from red to orange red |
| Fruit: firmness of flesh | Medium | Soft |
| Plant: size | Medium | Ranges from medium to large |
| Fruit: time of ripening | Very early | Medium |

TABLE 3

| Characteristic | 'PS-14.762.054' | 'PS-5016' (unpatented) |
|---|---|---|
| Fruit: firmness of flesh | Medium | Soft |
| Fruit: size | Large | Small |
| Plant: size | Medium | Large |
| Fruiting truss: position relative to foliage | Ranges from level with to below | Above |

BRIEF DESCRIPTIONS OF THE PHOTOGRAPHS

The accompanying color photographs illustrate the overall appearance of typical specimens of the new strawberry variety 'PS-14.762.054' at various stages of development, as true as it is reasonably possible with color reproductions of this type. Color in the photographs may differ slightly from the color value cited in the botanical descriptions which accurately describe the color of 'PS-14.762.054'. The depicted plant and plant parts of the new strawberry variety 'PS-14.762.054' are approximately seven to eight months old. The photographs were taken in Monterey County, California.

DETAILED BOTANICAL DESCRIPTION

Figure 1:
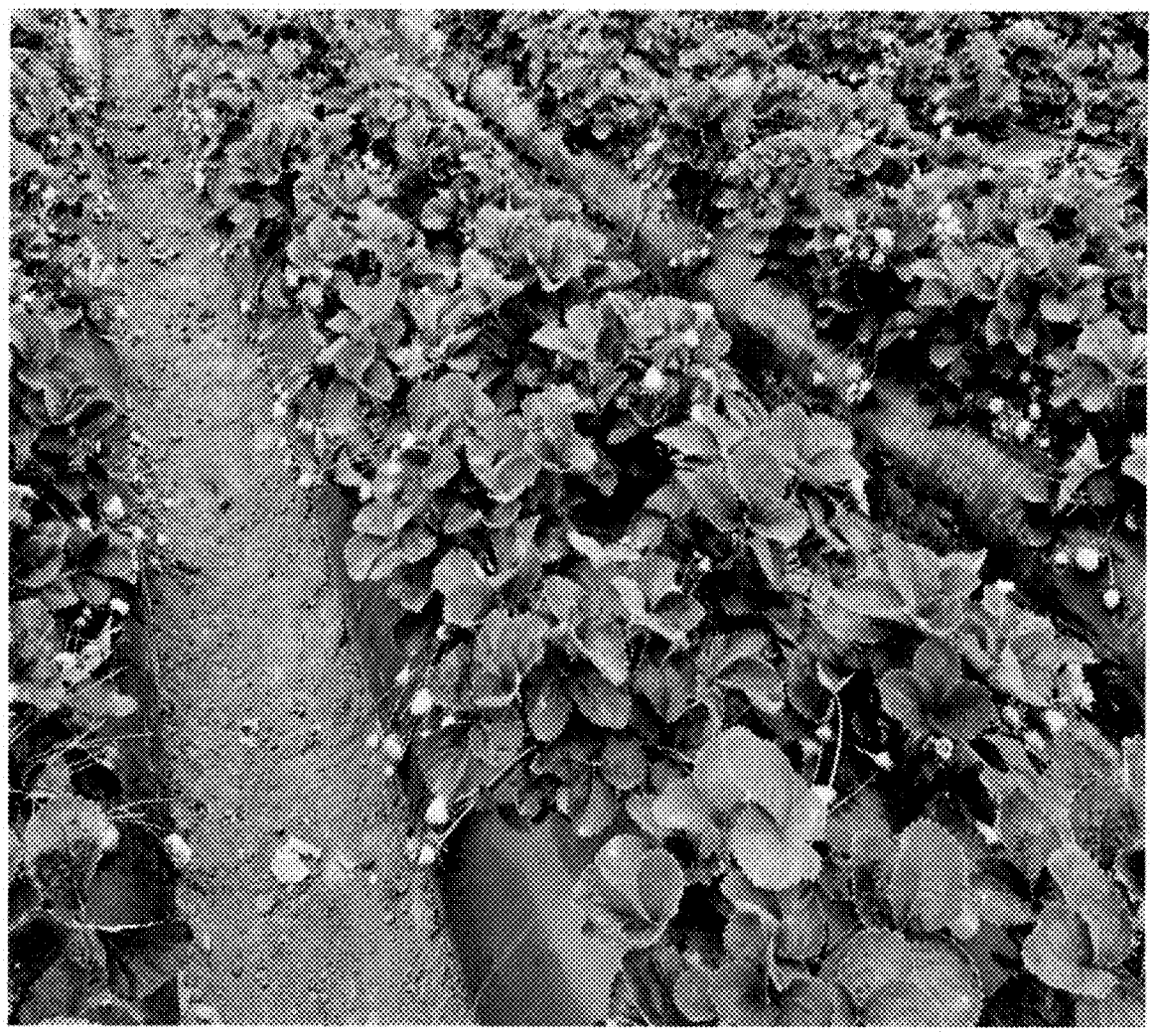
FIG. 1 shows fruiting field characteristics of 'PS-14.762.054', taken in the month of June 2023.
Figure 2:
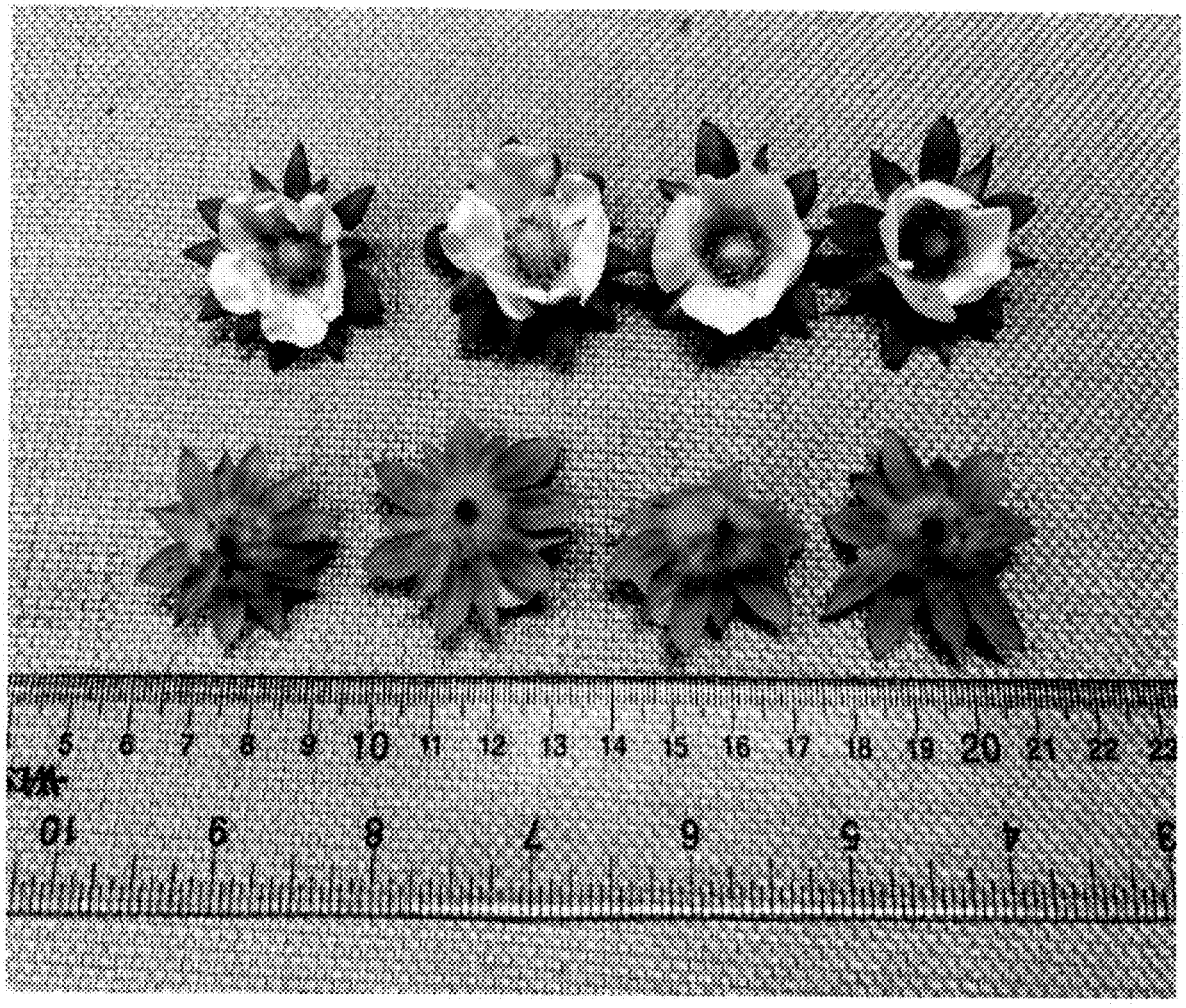
FIG. 2 shows upper and lower surfaces of flower and flower parts of 'PS-14.762.054', taken in the month of July 2023.
Figure 3:
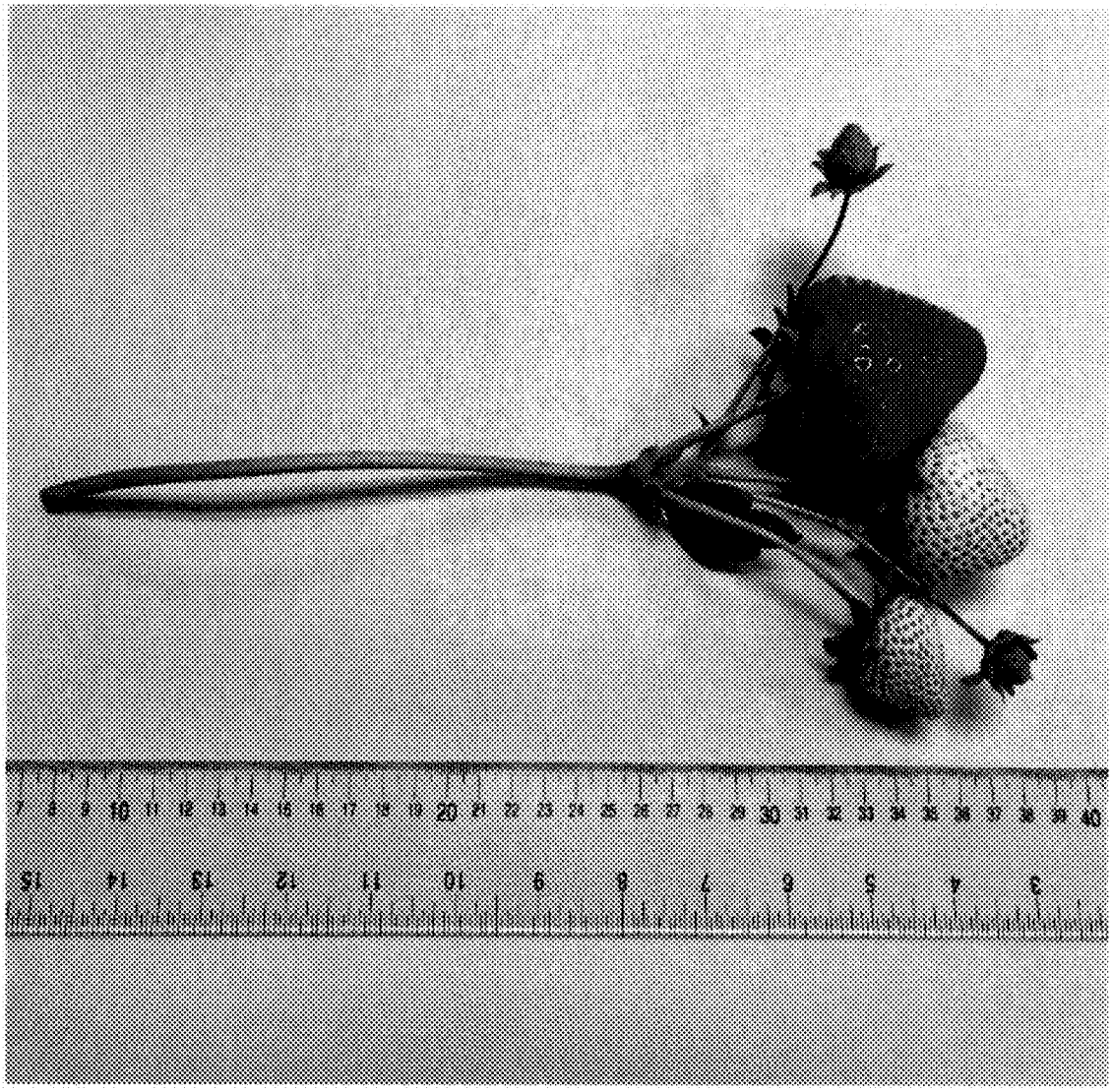
FIG. 3 shows typical fruiting truss and truss parts of 'PS-14.762.054', taken in the month of June 2023.
Figure 4:
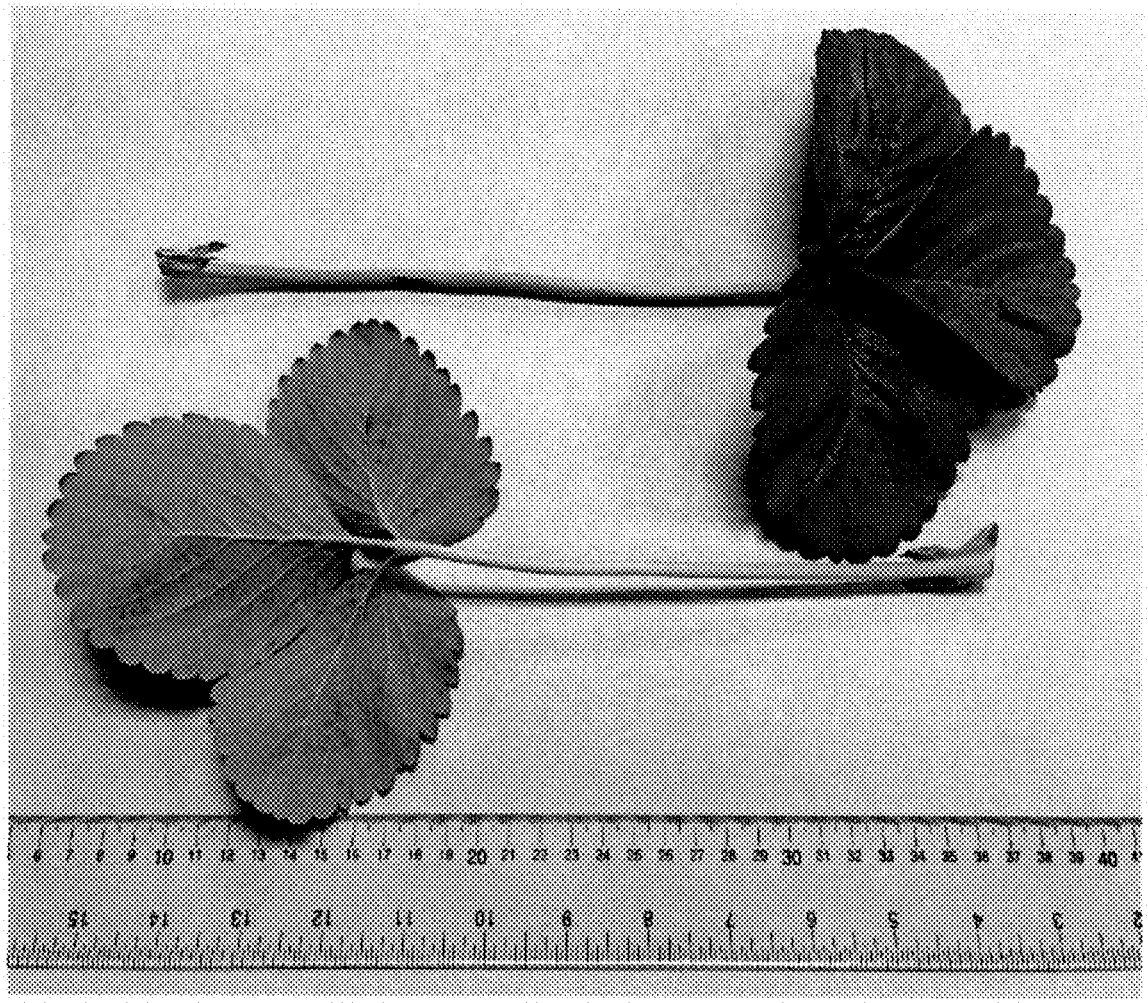
FIG. 4 shows upper and lower surfaces of leaf and leaf parts of 'PS-14.762.054', taken in the month of June 2023.
Figure 5:
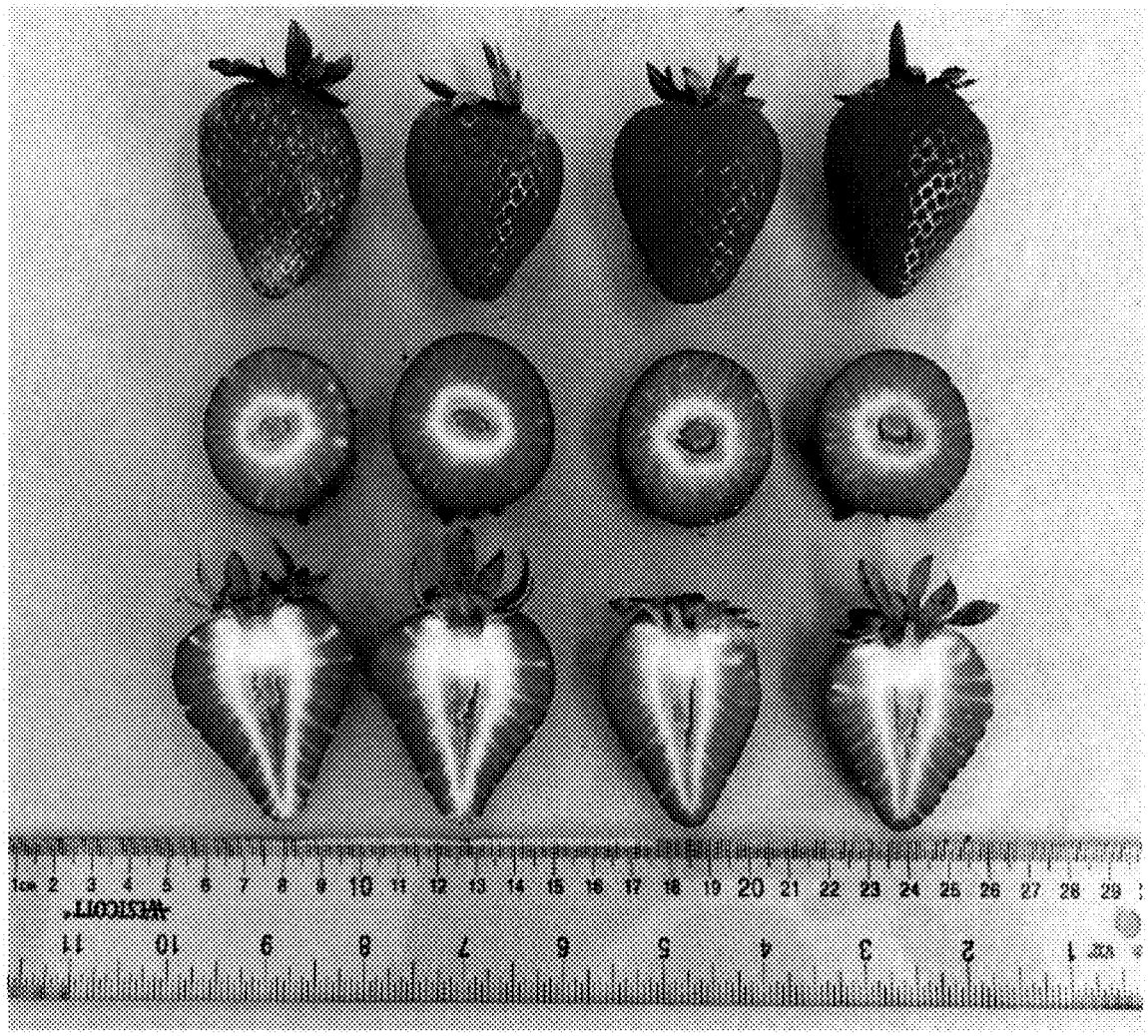
FIG. 5 shows internal and external mature fruit characteristics of 'PS-14.762.054', taken in the month of July 2023.

The new variety 'PS-14.762.054' has not been observed under all possible environmental conditions. The characteristics of the new variety 'PS-14.762.054' may vary in detail, depending upon variations in environmental factors, including weather (temperature, humidity and light intensity), day length, soil type and location. In addition, the characteristics of any parental variety or comparison variety included in Tables 1, 2 and 3 of the present invention may vary in detail, depending upon variations in environmental factors, including weather (temperature, humidity and light intensity), day length, soil type and location.

The aforementioned photographs, together with the following description of the new variety 'PS-14.762.054', unless otherwise noted, are based on observations taken during the 2023 growing season in Monterey County, California. These measurements and ratings were taken from plants of 'PS-14.762.054' dug from a high-elevation nursery located in Siskiyou County, California during mid-October 2022 and planted approximately three to four weeks later in Monterey County, California. The approximate age of the observed plants is seven to eight months. Yield observations including average weight and marketable yield, along with fruit quality characteristics including soluble solids, are averaged from four years of data collected from the 2019 through 2022 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London (2007).

The following characteristics describe fruit, plant, stolon, foliage, fruiting truss, flower, reproductive organs and pest and disease characteristics of the new strawberry 'PS-14.762.054'.

Fruit characteristics:

*Color of mature fruit*.—RHS N45A (red).

*Color of internal flesh (excluding core)*.—RHS 43A (medium red).

*Color of core*.—RHS 43B (light red).

*Fruit average length (cm)*.—4.7.

*Fruit average width (cm)*.—4.0.

*Fruit size*.—Large.

*Average length/width ratio*.—1.16 (slightly longer than broad).

*Hollow center average length (mm)*.—14.3.

*Hollow center average width (mm)*.—4.4.

*Hollow center expression*.—Weak.

*Season average weight (gm)*.—31.9.

*Season marketable yield (gm/plant)*.—1,625.

*Predominant shape*.—Conical.

*Difference in shape between primary and secondary fruit*.—None or very slight.
*Band without achenes*.—Narrow.
*Evenness of surface*.—Even or very slightly uneven.
*Evenness of color*.—Even or very slightly uneven.
*Glossiness*.—Medium.
*Insertion of achenes*.—Level with surface.
*Average calyx diameter* (*cm*).—4.5.
*Position of calyx attachment*.—Ranges from inserted to level.
*Attitude of sepals*.—Ranges from outward to upward.
*Size of calyx in relation to fruit diameter*.—Slightly larger.
*Adherence of calyx* (*when fully ripe*).—Strong.
*Firmness of flesh*.—Medium.
*Keeping quality*.—Very good.
*Fruit market*.—Fresh.
*Post-harvest fruit longevity* (*at* 1-3 *degrees celsius*).—7 to 10 days.
*Distribution of red color of the flesh*.—Marginal and central.
*Flavor*.—Very good.
*Soluble solids* (% *brix*).—7.5.
*Achene color, shaded side*.—RHS 162B (greyed yellow group).
*Achene color, sun-exposed side*.—RHS 182A (greyed red group).
*Average achene length* (*mm*).—1.6.
*Average achene width* (*mm*).—0.8.
*Average achene weight* (*mg*).—0.51.
*Average achenes per berry*.—408.
*Achene shape*.—Elliptic.
*Time of beginning flowering*.—Very early (March in Monterey County, California).
*Time of beginning of fruit ripening*.—Very early (April in Monterey County, California).
*Flowering season*.—March to October (in Monterey County, California).
*Harvest season*.—April to November (in Monterey County, California).
*Harvest maturity*.—July (in Monterey County, California).
*Plant hardiness*.—Zone 10 (on USDA plant hardiness zone map).
*Type of bearing*.—Non-remontant (summer-bearer).

Plant characteristics:
*Average height* (*cm*).—30.8.
*Average spread* (*cm*).—36.3.
*Size*.—Medium.
*Habit*.—Upright.
*Density*.—Ranges from sparse to medium.
*Vigor*.—Medium.

Stolon characteristics:
*Color*.—RHS 146D (yellow green group).
*Anthocyanin coloration*.—RHS 181D (greyed red group).
*Anthocyanin intensity*.—Ranges from weak to medium.
*Pubescence*.—Sparse.
*Attitude of hairs*.—Upward.
*Average quantity in nursery* (*per square foot*).—8 to 12 (ranges from medium to many).
*Average diameter at the bract* (*mm*).—3.4 (medium).
*Length from mother plant to first daughter* (*cm*).—34.3.

Terminal leaflet characteristics:
*Average length* (*cm*).—9.0.
*Average width* (*cm*).—9.1.
*Average area terminal* ($cm^2$).—82.1.
*Average length/width ratio*.—0.99 (as long as broad).
*Shape of base*.—Obtuse.
*Shape of apex*.—Obtuse.
*Margins* (*shape of teeth*).—Obtuse (serrate to crenate).
*Average serrations per leaf*.—20.3.

Foliage characteristics:
*Color of upper surface*.—RHS 146A (medium yellow green).
*Color of lower surface*.—RHS 147C (yellow green group).
*Color of venation, upper surface*.—RHS 146D (yellow green group).
*Color of venation, lower surface*.—RHS 145A (yellow green group).
*Number of leaflets*.—3.
*Leaf size*.—Large.
*Average length* (*cm*).—15.9.
*Average width* (*cm*).—18.1.
*Average area foliage* ($cm^2$).—289.3.
*Shape in cross section*.—Slightly concave to flat.
*Interveinal blistering*.—Medium.
*Texture, upper surface*.—Medium.
*Texture, lower surface*.—Smooth.
*Venation pattern*.—Pinnate reticulate.
*Leaf glossiness*.—Medium.
*Leaf variegation*.—Absent.

Petiole characteristics:
*Petiole color*.—RHS 144B (yellow green group).
*Petiole average length* (*cm*).—21.4.
*Petiole average diameter* (*mm*).—4.3.
*Average size*.—Long.
*Attitude of hairs*.—Slightly outward.
*Frequency of bract leaflets*.—Few (5% occurrence).
*Size of bract leaflets*.—Small.
*Pubescence*.—Moderate.
*Petiolule color*.—RHS 144B (yellow green group).
*Petiolule average length* (*mm*).—11.8.
*Petiolule average diameter* (*mm*).—2.2.

Stipule characteristics:
*Color*.—RHS 146C (yellow green group).
*Anthocyanin coloration*.—RHS 60C (red purple group).
*Anthocyanin intensity*.—Medium.
*Average length* (*mm*).—19.4.
*Average width* (*mm*).—9.8.
*Shape*.—Triangular.
*Texture*.—Light.
*Shape of base*.—N/A.
*Shape of apex*.—Acuminate.
*Margins*.—Entire (smooth).

Fruiting truss characteristics:
*Anthocyanin coloration*.—RHS 183B (greyed purple group).
*Anthocyanin intensity*.—Strong.
*Average length at maturity* (*cm*).—31.4.
*Position relative to foliage*.—Ranges from beneath to level with.
*Flower quantity* (*average per plant season long*).—60 to 70 (medium).
*Fruit quantity per truss*.—5.3 (medium).
*Attitude at first pick*.—Prostrate.
*Primary pedicel color*.—RHS 144A (yellow green group).

*Primary pedicel length* (*cm*).—6.2.
*Primary pedicel diameter* (*mm*).—3.1.
*Pedicel attitude of hairs*.—Upward.
*Pedicel texture*.—Weak.
*Primary peduncle color*.—RHS 144A (yellow green group).
*Primary peduncle length* (*cm*).—15.8.
*Primary peduncle diameter* (*mm*).—4.9.
*Peduncle texture*.—Medium.

Flower characteristics:
*Petal color, upper surface*.—RHS NN155C (white group).
*Petal color, lower surface*.—RHS NN155C (white group).
*Petal average length* (*mm*).—14.0.
*Petal average width* (*mm*).—14.2.
*Petal average length/width ratio*.—0.99 (as long as broad).
*Average petals per flower*.—5.6.
*Petal shape*.—Obovate.
*Petal texture*.—Smooth.
*Petal shape of base*.—Obtuse.
*Petal shape of apex*.—Rounded.
*Petal margins*.—Entire (smooth).
*Sepal color, upper surface*.—RHS 137C (green group).
*Sepal color, lower surface*.—RHS 138B (green group).
*Sepal average length* (*mm*).—14.0.
*Sepal average width* (*mm*).—6.2.
*Sepal average length/width ratio*.—2.28.
*Average sepals per flower*.—11.6.
*Sepal shape*.—Elliptical.
*Sepal texture*.—Light.
*Sepal shape of apex*.—Acute.
*Sepal margins*.—Entire (smooth).
*Corolla* (*flower*) *average diameter* (*mm*).—35.3 (large).
*Average flower depth* (*mm*).—17.0 (deep).
*Calyx average diameter* (*mm*).—38.9.
*Size of calyx relative to corolla*.—Larger.
*Size of inner calyx relative to outer calyx*.—Smaller.
*Arrangement of petals*.—Overlapping.

Reproductive organs:
*Anther color*.—RHS 16A (yellow orange group).
*Filament color*.—RHS 145C (yellow green group).
*Stamen*.—Present.
*Filament average length* (*mm*).—2.2.
*Anther average length* (*mm*).—1.2.
*Anther average width* (*mm*).—0.8.
*Anther shape*.—Elliptic.
*Pollen amount*.—Abundant.
*Ovary color*.—RHS 147C (yellow green group).
*Style color*.—RHS 151C (yellow green group).
*Pistil average quantity per flower*.—408.
*Pistil average length* (*mm*).—1.3.
*Stigma average diameter* (*mm*).—0.3.
*Stigma shape*.—Rounded.

Disease and pest reactions:
*Powdery mildew* (*sphaerotheca macularis*).—Moderate.
*Botrytis fruit rot* (*botrytis cinerea*).—Moderately susceptible.
*Fusarium wilt* (*fusarium oxysporum*).—Resistant.
*Two-spotted spider mite* (*tetranychus urticae*).—Moderately susceptible.

We claim:

1. A new and distinct strawberry plant named 'PS-14.762.054', as herein described and illustrated by the characteristics set forth above.

* * * * *